United States Patent [19]

McCue et al.

[11] Patent Number: 5,570,895
[45] Date of Patent: Nov. 5, 1996

[54] REMOTE AIR TRANSPORT TRUCK

[76] Inventors: Patrick O. McCue, 2108 W. Virginia Ave., Phoenix, Ariz. 85009; Nedward B. Dunnington, 20512 W. Lower Buckeye Rd., Buckeye, Ariz. 85326; David Rozzen, 820 E. Vineyard, Phoenix, Ariz. 85040

[21] Appl. No.: 380,290

[22] Filed: Jan. 30, 1995

[51] Int. Cl.[6] .................................................. B62B 1/16
[52] U.S. Cl. .................................. 280/47.19; 280/47.26; 280/79.6; 280/47.33
[58] Field of Search .............................. 280/37, 42, 652, 280/47.18, 47.19, 47.26, 47.31, 47.32, 47.33, 79.6, 770; D12/95; 137/581

[56] References Cited

U.S. PATENT DOCUMENTS

| | | | |
|---|---|---|---|
| 1,244,030 | 10/1917 | Cave | 280/47.26 X |
| 2,667,397 | 1/1954 | Hallisey | 280/47.26 X |
| 3,162,361 | 12/1964 | Brighton et al. | 280/47.26 X |
| 4,253,716 | 3/1981 | Turner, Jr. | 280/47.26 X |
| 4,625,949 | 12/1986 | Walker | 280/47.19 X |
| 5,207,723 | 5/1993 | Newby, Sr. | 280/47.19 X |
| 5,431,422 | 7/1995 | Gamache | 280/47.19 |
| 5,492,346 | 2/1996 | Stadler et al. | 280/79.6 X |

FOREIGN PATENT DOCUMENTS 1539021  1/1979  United Kingdom ............... 280/37

*Primary Examiner*—Brian L. Johnson
*Attorney, Agent, or Firm*—Warren F. B. Lindsley

[57] ABSTRACT

A truck containing air cylinders and associated pressure control and delivery apparatus for use in supplying breathing air and air for tool operation in remote rescue operations. The truck is shielded for protection of its equipment against damage due to impact. Separate breathing air and tool air regulation and delivery channels are incorporated.

6 Claims, 5 Drawing Sheets

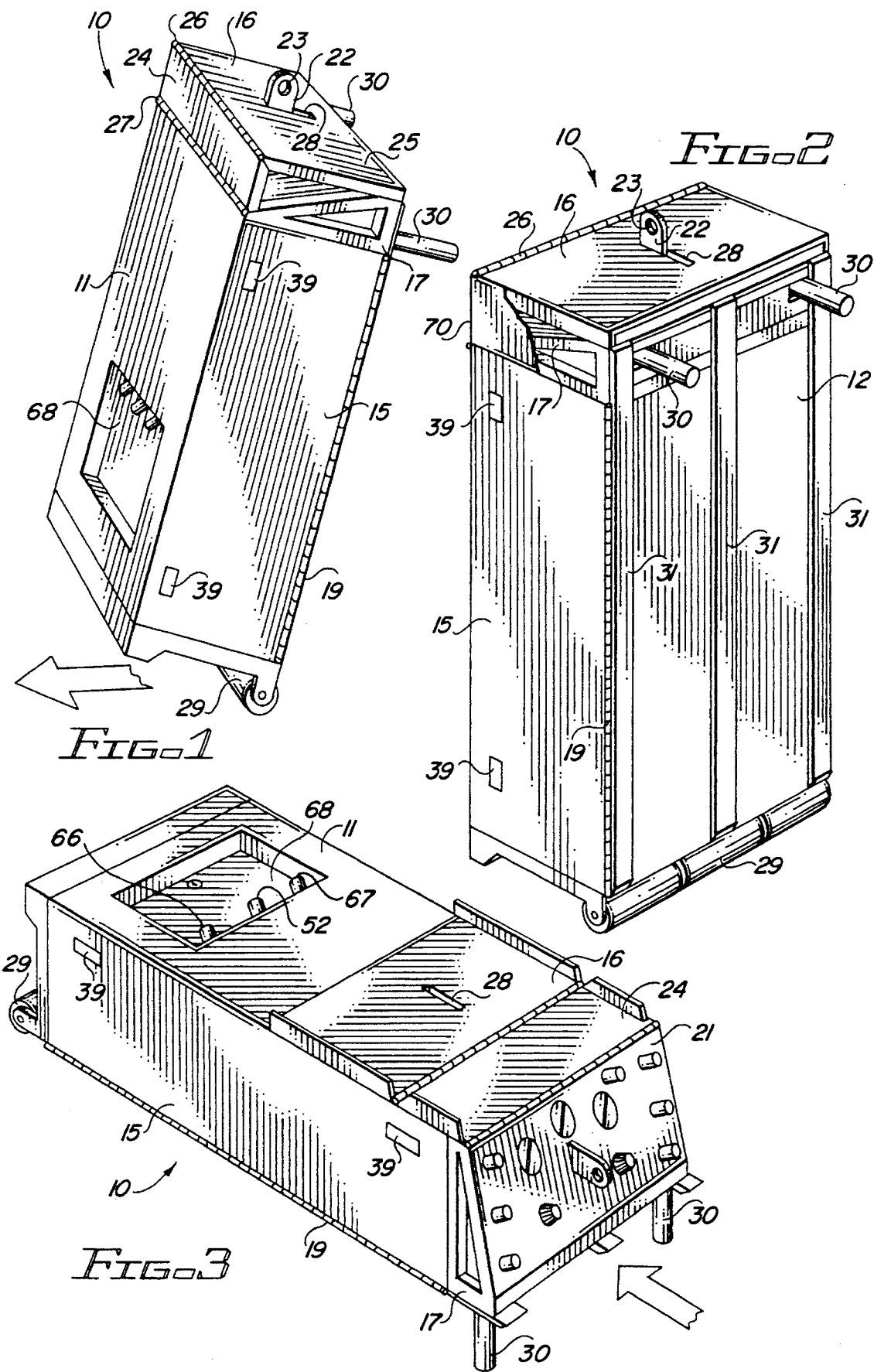

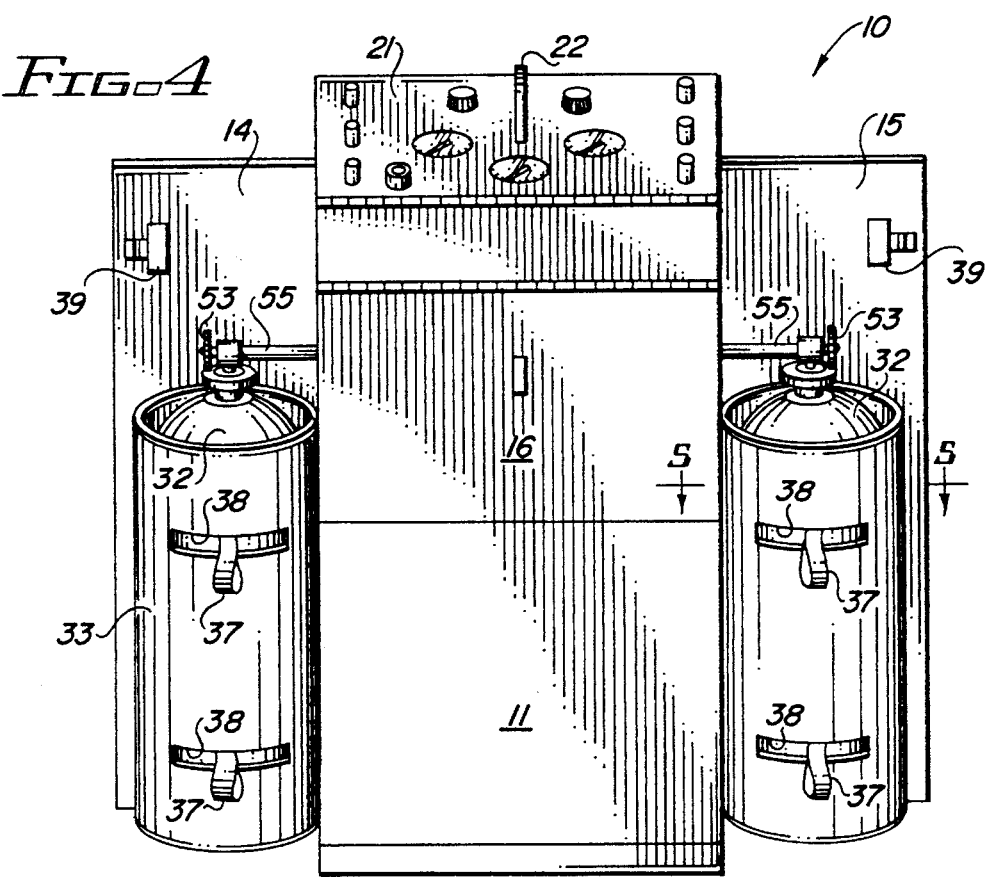
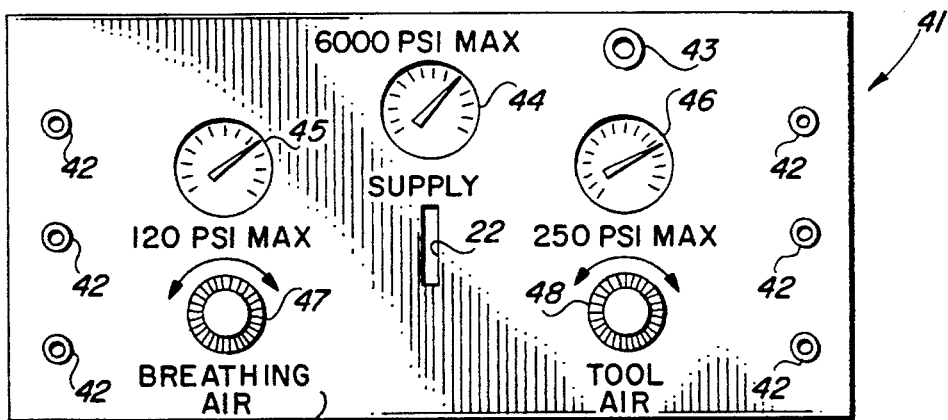
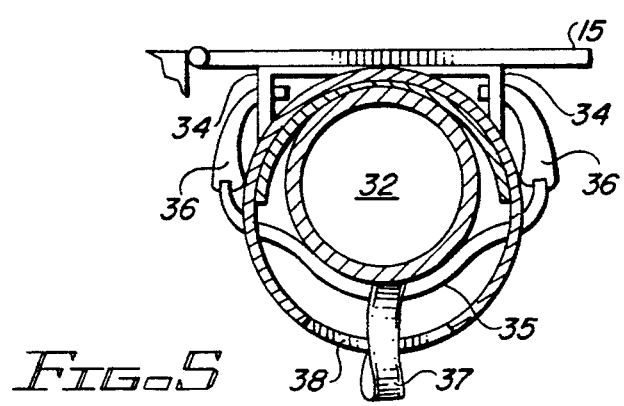

REMOTE AIR TRANSPORT TRUCK

BACKGROUND OF THE INVENTION

This invention relates to apparatus for transporting compressed air cylinders to a given site and more particularly to dispensing a continuous air supply to emergency rescue sites or confined spaces, as defined by OSHA, that are frequently impossible to reach except with portable equipment.

DESCRIPTION OF THE PRIOR ART

Remote air supply carts or trucks of various types are employed by firefighters and other emergency rescue personnel in search and rescue operations requiring entry into confined spaces where the air supply is inadequate or contaminated as well as industrial application where workers operate in confined spaces. Various forms of equipment are used to supply air to such individuals as well as providing a compressed air source for the operation of various cutting tools, air hammers etc. used for breaking through barriers and freeing trapped victims of cave-ins or collapsed structures.

Currently available equipment of this type has saved many lives. In numerous emergency situations, rescue operations could not have succeeded without it. There are, however, a number of deficiencies and limitations in the present equipment that need to be corrected.

A first and very important deficiency is the lack of protection of the equipment against damage to exposed gauges, valves and other critical parts of the apparatus that can readily be incurred as the result of impact with surrounding obstacles. The cart or truck when being moved through confined spaces with limited lighting and visibility is susceptible to damage. This poses a very serious hazard and risk that the equipment may not be operable by the time it reaches the victim.

A second deficiency that is generally present in such equipment is the lack of separate air manifolds for breathing air and for tool operation. As a source for breathing air the pressure should be regulated to 120 psi or less; for tool operation higher pressures (12–250 psi) are preferred. Because both air sources are commonly required at the same time, it is not always possible to adjust pressure for the instant application, and with simultaneous use a compromise between the two preferred pressures means less than ideal conditions for one or both uses. Excessive pressure to a face mask can also rupture its diaphragm.

Some prior art equipments also fail to give attention to the importance of guarding against accidental ignition of combustible atmospheres. If the truck is constructed of steel it can produce sparks when it strikes a rock or other hard surface during transport. Using such a truck in a combustible atmosphere can therefore be quite hazardous.

Another deficiency of the prior art equipment is that the remote air system is limited to the amount of compressed air contained in the cylinders and the size of the cylinders is limited to the conventional wheels that are used on the truck. With conventional wheels, the cart is difficult to maneuver over the rough and irregular surfaces that are frequently encountered in rescue operations.

SUMMARY OF THE INVENTION

In accordance with the invention claimed, a remote air transport cart or truck is provided in a novel construction that overcomes the deficiencies and limitations of prior art equipment.

It is, therefore, one object of this invention to provide an improved remote air transport truck for use in emergency rescue operations and for various industrial application.

Another object of this invention is to provide such a remote air transport truck with protective shields that guard against damage to critical parts of the equipment during transport through constricted passageways to the emergency destination or work area for industrial application.

A further object of this invention is to provide in such an air transport truck separate manifolds for breathing air and for tool operation with the pressures separately regulated to the proper levels for each application.

A still further object of this invention is to provide such an air transport truck with improved maneuverability by virtue of its use of a solid rubber roller resistant to corrosives in place of conventional wheels for rolling support.

A still further object of this invention is to provide such an air transport truck incorporating all of the aforementioned improved characteristics while maintaining dimensions that allow passage through manholes and other restricted openings.

Still another object of this invention is to provide an air transport truck to be used as a filling station by fire fighters who may hook up their tanks to outlets provided on the front of the truck for transfilling their air bottles.

A further object of this invention is to provide a continuous and uninterrupted air supply from a remote/supply or source i.e., compressor or high volume cylinders. This is accomplished through the state of the art quick connections engineered into the air circuit.

Yet another object of this invention is the capability to supply additional trucks with a continuous air source. A series connection of trucks allows multiple teams/tools to operate in unison.

Yet another modification is the use of air filled gauges instead of oil filled. This safety feature will prevent chemical reactions that may be caused if gauge breakage were to occur in certain atmospheric conditions.

A further object of this invention is to provide a continuous and uninterrupted air supply from a remote air supply or source, i.e. compressor or high volume cylinders.

Further objects and advantages of the invention will become apparent as the following description proceeds and the features of novelty which characterize this invention will be pointed out with particularity in the claims annexed to and forming a part of this specification.

BRIEF DESCRIPTION OF THE DRAWINGS

The present invention may be more readily described with reference to the accompanying drawings in which:

FIG. 1 is a perspective view of the remote air supply truck of the invention, with the truck shown in position for being moved from one location to another.

FIG. 2 is a perspective view showing the rear and one side of the air supply truck with the truck standing in an upright position;

FIG. 3 is a perspective view of the air supply truck with the truck resting on its rollers and hand grips, this constituting its preferred operational position in cramped quarters that afford limited headroom;

FIG. 4 is a perspective view of the air supply truck taken from the front of the truck with both side doors open and showing the air canisters mounted on the doors;

FIG. 5 is a cross-sectional view taken along line 5—5 of FIG. 4 and illustrating the means employed to secure the air canisters within the door-mounted protective canister containers;

FIG. 6 is a plan view of the control and instrument panel as organized for a first embodiment of the invention;

DESCRIPTION OF THE PREFERRED EMBODIMENT

Figure 7:
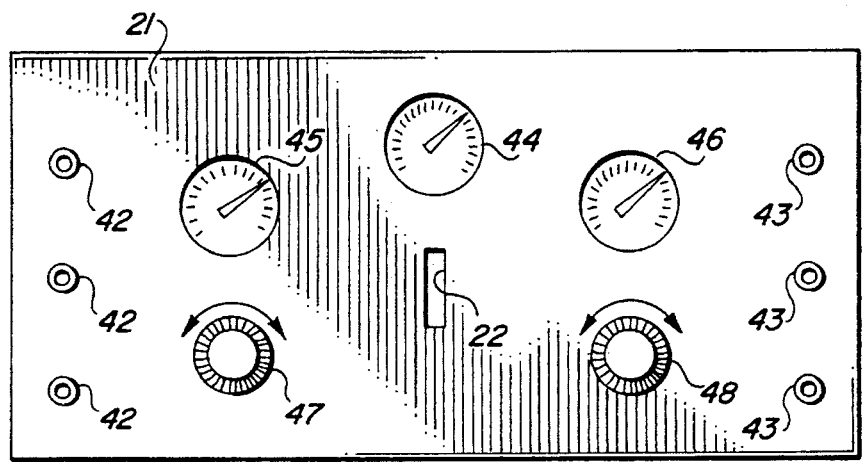
FIG. 7 is a plan view of the control and instrument panel as organized for a second embodiment of the invention.

Referring more particularly to the drawings by characters of reference, FIGS. 1–4 and FIG. 8 disclose the mechanical construction of the remote air supply cart or truck 10 of the invention.

As shown in the drawings, truck 10 provides a protective enclosure comprising a fixed front panel 11, a fixed rear panel 12, a bottom panel 13, hinged side doors 14 and 15, and a double-hinged top cover 16. The individual parts of the enclosure are made of sheet aluminum or other relatively soft material which does not produce sparks when impacted by rocks or other hard surfaces, all hardware fasteners are stainless steel or brass.

The front, rear and bottom panels, 11, 12 and 13, are secured to an aluminum frame 17 which is partially exposed in FIGS. 1, 2, 3 and 8. The side doors 14 and 15 are secured along their rear edges to the adjoining edges of rear panel 12 by piano hinges 18 and 19.

Figure 8:
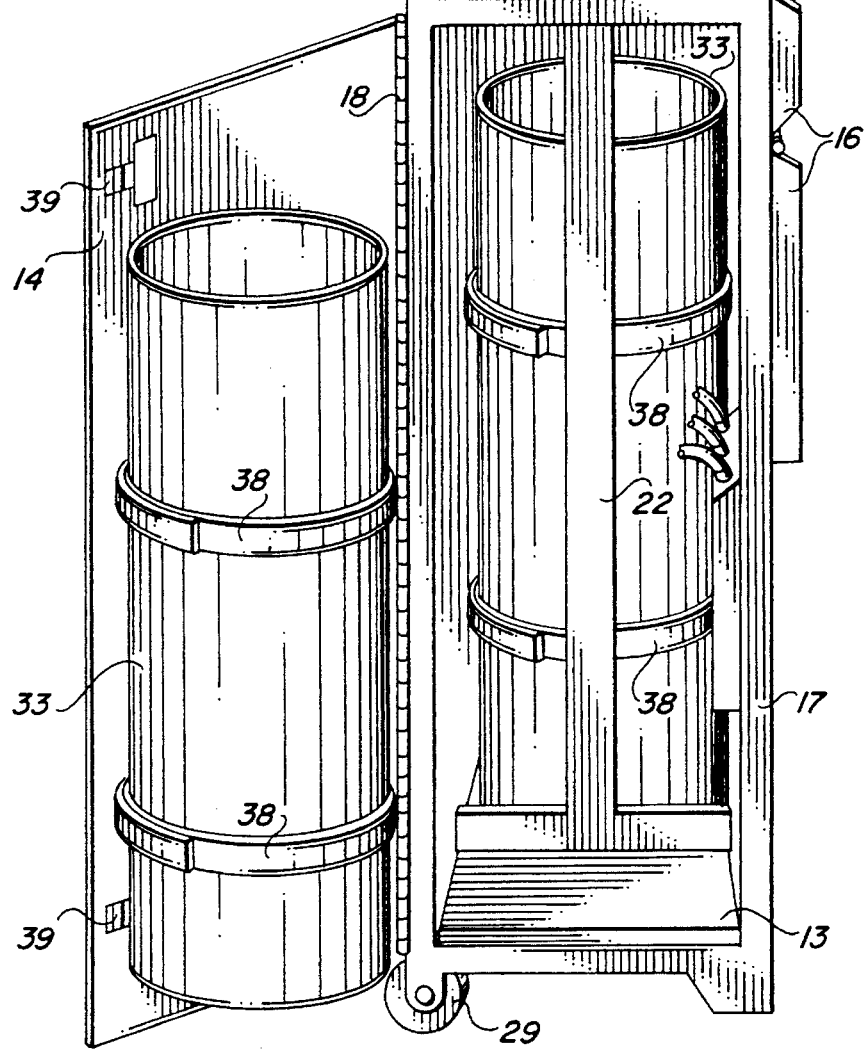
FIG. 8 is a perspective view of the air supply truck of the invention as seen from one side of the truck with the door open.

As shown more clearly in FIG. 8, the upper end of the enclosure is inclined to provide a sloping surface 21 on which are mounted air pressure controls, air pressure gauges and fittings for the attachment of air hoses. Rigidly attached to frame 17 is a lifting bar 22 which rises from a lower frame attachment near the base of the frame and passes through an opening in the center of surface 21. The protruding upper end of bar 22 has an opening 23 for attachment to a hoisting cable by means of which the truck may be lowered through a vertical passageway.

The double-hinged cover 16 when in its closed position as shown in FIGS. 1 and 2 provides a protective covering for the controls, gauges and fittings mounted on surface 21. To facilitate this function, cover 16 is formed by two parts including a narrow parallel extending panel 24 and a laterally extending panel 25 with respect to the longitudinally axis of the truck. These two panels are attached to each other at their adjoining edges by a piano hinge 26. Panel 24 is attached at its edge opposite hinge 26 to the upper edge of front panel 11 by another piano hinge 27. Hinge 27 also lies along the lower front edge of sloping surface 21. When cover 16 is closed, as shown in FIG. 1, and truck 10 is sitting upright as shown in FIG. 2, panel 24 rises from the front edge of surface 21 thereto to a height level with the higher rear edge of surface 21. From the upper edge of panel 24, panel 25 extends perpendicularly across the top of surface 21. As cover 16 is being moved to its closed position, the upper end of bar 22 passes through a slotted opening 28 in the center of panel 25. Bar 22 and the mating opening 28 serve as a latching mechanism that secures cover 16 in its closed position. In its open position, cover 16 hangs down over front panel 11 as shown in FIGS. 3, 4 and 8.

To facilitate moving the truck over rough or rocky surfaces, cart 10 is equipped with solid rubber rollers 29 and handles 30 with the rollers being resistive to acids and corrosive gases.

As shown in FIG. 2, the three-section roller 29 is positioned below the lower edge of rear panel 12. Two handles 30 extend perpendicularly rearward from the upper corners of panel 12 so that a person moving the truck can grasp the two handles and push or pull truck 10 as one would push a wheelbarrow. The rollers are found to provide easier passage over bumps and crevices that are difficult to negotiate with conventional wheels.

Handles 30 have rubber grips and are attached to the truck by means of threaded studs that extend from the attached ends into threaded holes in frame 17. The handles are thus readily removable when it becomes necessary for passage through a small opening.

The rear panel 12 is protected against damage while the truck is being moved over sharp edges by three runners 31. As shown in FIG. 2, two of the runners 31 are positioned lengthwise along the outer vertical edges and one at the center of panel 12.

In use at the emergency location, truck 10 may be accessed or operated in an upright position as shown in FIGS. 2 and 4 or in the lowered horizontal position shown in FIG. 3. In the horizontal position, truck 10 rests on roller 29 and on handles 30. In this position, sloping surface 21 of the control panel provides improved visibility of gauges and controls for the operation.

Two air cylinders comprising canisters 32 are mounted inside protective containers 33 that are secured by means of brackets 34 shown in FIG. 5 to the inside surfaces of side doors 14 and 15. The cylinders and their containers swing out for easy access when the doors are opened as shown in FIG. 4. Containers 33 are made of a tough synthetic material that protects the cylinders against damage while the doors are open.

Cylinders 32 are secured within the containers by means of two elastic bands 35, one near the top and one near the bottom of the cylinders. The elastic bands 35 encircle cylinder 32, as shown in FIG. 5, their ends secured to mounting brackets 34 by plastic attachment members 36. During installation and removal of the cylinders from the containers, the elastic bands 35 are pulled away from the cylinders by means of nylon straps 37 that are looped around bands 35 and extend through slotted openings 38 in the walls of containers 33.

Side doors 14 and 15 are held closed by latches 39, two located on each door.

Control panel 41 on surface 21 is shown in FIG. 6 as seen by the operator when truck 10 is resting in the horizontal position shown in FIG. 3. Incorporated in control panel 41 are six breathing air outlets 42, one tool air outlet 43, three pressure gauges including a high pressure gauge 44 for the primary air supplied from the air cylinders, a low pressure gauge 45 for breathing air pressure, and an intermediate pressure gauge 46 for tool air pressure, a breathing air pressure control 47, and a tool air pressure control 48. Controls 47 and 48 may be adjusted to set breathing air and tool air, respectively to the appropriate levels up to 120 psi maximum for breathing and between 120 to 250 psi maximum for tool operation. PSI means pounds per square inch of pressure.

For certain applications a greater number of tool outlets will be found appropriate. In such cases a modified control panel 41' may be employed as shown in FIG. 7. In this case three breathing air outlets 42 and three tool air outlets 43 are provided.

Figure 9:
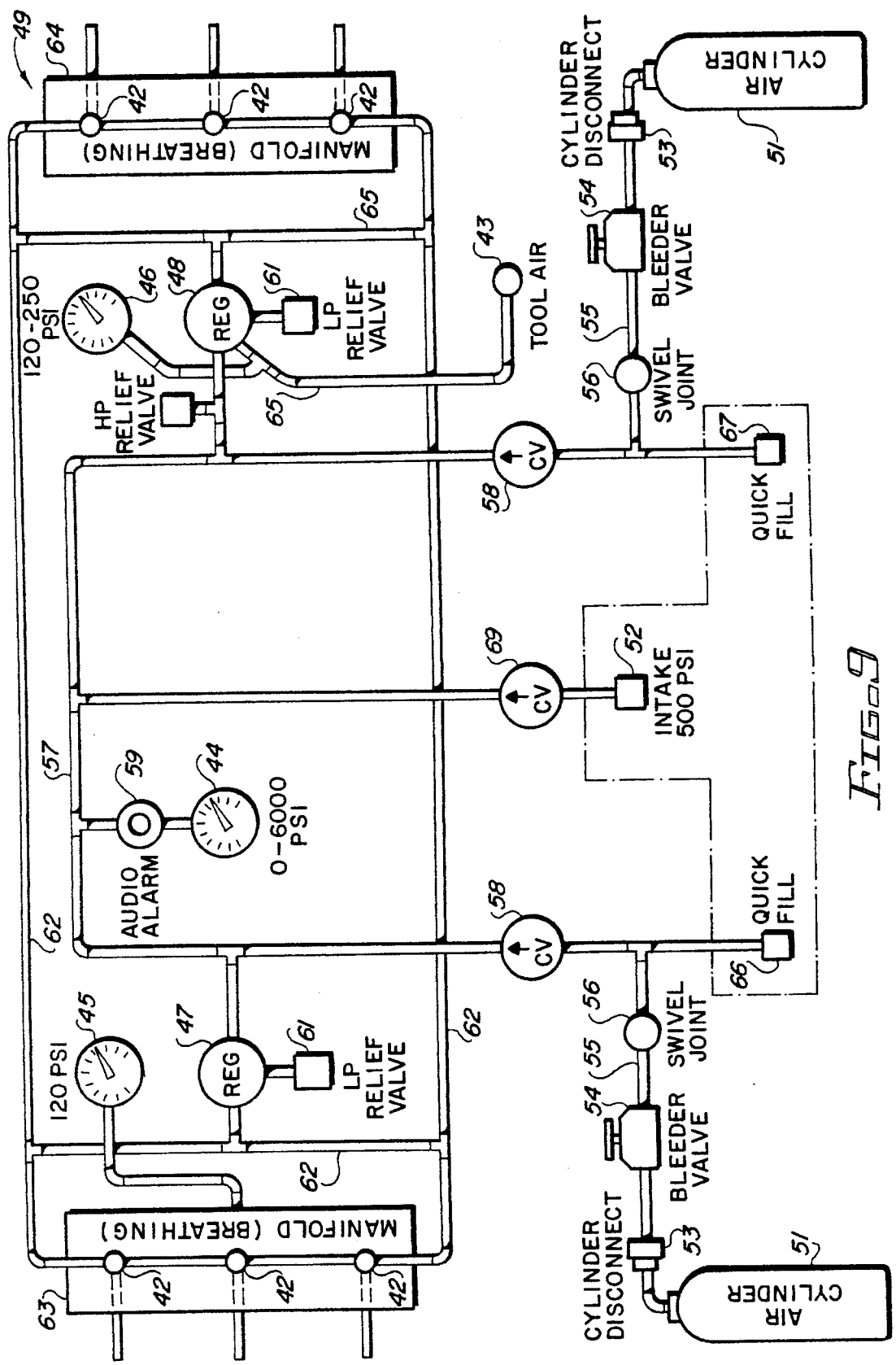
FIG. 9 is a schematic illustrating the interconnections of the gauges, controls and fittings comprising the air control system of the remote air transport truck for the first embodiment of the invention.

FIG. 9 is a schematic showing the elements of the pressure control and delivery system 49. Included in system 49 are the gauges, controls and outlets already described in connection with control panel 41. In FIG. 9, air pressure controls 47 and 48 are more specifically identified as regulators (REG), but they are actually one and the same.

Air is supplied to system 49 from one or both of the air cylinders 51 or from an external high pressure line via intake port 52. Conventional couplings or disconnects 53 connect the cylinders to the high pressure lines of system 49. Immediately downstream from disconnects 53 are bleeder valves 54, incorporated for the purpose of bleeding off pressure prior to a disconnection from the cylinder. Because the connections to the cylinders are made via flexible air hoses 55 (see also FIG. 4) to permit mounting the cylinders on the side doors, swivel joints 56 are incorporated in series.

Downstream from the swivel joints, air from the cylinders enter the high pressure distribution lines 57 via check valves 58. The check valves 58 are one-way valves that prevent momentary loss of pressure in the distribution system during the disconnection of one of the air cylinders. Air pressure in the high pressure distribution lines is displayed by air filled gauges 44. A low pressure condition in these lines indicative of impending problems due to depletion of the air supply is signaled by an audio alarm 59.

From the high pressure lines 57 high pressure air enters the controls or regulators 47 and 48, each of which is equipped with a low pressure relief valve 61. The relief valves relieve pressure on the low pressure side of the regulators in the event of a regulator malfunction that produces hazardous pressure levels in the low pressure lines.

From the low pressure side of regulator 47 air is delivered, at up to 120 psi maximum, via low pressure lines 62 to breathing air manifolds 63 and 64 which feed the six breathing air outlets 42. The pressure in these lines is adjustable by means of regulator 47 and the instant pressure is displayed by gauge 45.

From the low pressure side of regulator 48, tool air is delivered via high pressure line 65 to tool air outlet 43 at a variable 120 to 250 psi. Tool air pressure is adjustable by means of regulator 48 and is displayed by gauge 46.

As mentioned earlier, system 49 may also be supplied from an external high pressure line. Intake port 52 is incorporated for this purpose. Port 52 and two quick fill ports 66 and 67 are located in a recessed connector panel 68 in the front panel 11 of truck 10 as shown in FIGS. 1 and 3. Air from the external high pressure line entering at port 52 passes through a check valve 69 into the high pressure lines 58.

Quick fill ports may be used to supply air for other users from air cylinders 51, or they may be used to introduce air into system 49 from another source in an emergency situation.

Figure 10:
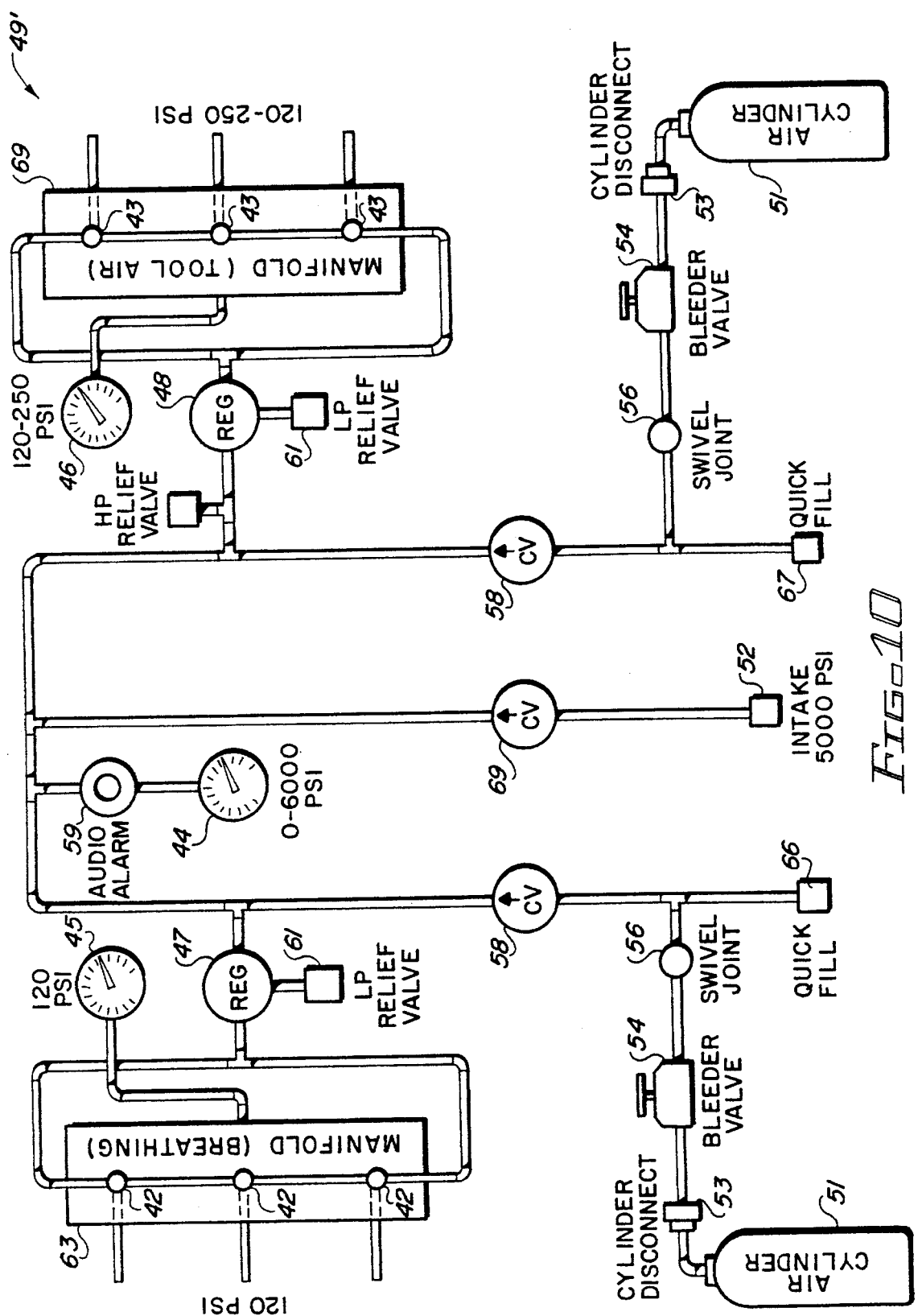
FIG. 10 is a schematic of the air control system for the second embodiment of the invention.

An alternate distribution and control system 49' corresponding to control panel 49 is shown in FIG. 10. Control system 49' is the same as control system 49 except that control system 49' has only one breathing air manifold 63 with three breathing air outlets 42 and it has a tool air manifold 69 with three tool air outlets 43. As in the case of system 49, breathing air pressure and tooling air pressure are separately regulated and controlled.

It should be noted that truck 10 is covered by a metallic housing comprising fixed front panel 11, fixed rear panel 12, bottom panel 13, hinged side doors 14 and 15 and a double-hinged top cover 16. Any exposed opening in the enclosure are covered by a panel 70 as shown in FIG. 2.

Although but two embodiments of the invention have been illustrated and described, it will be apparent to those skilled in the art that various changes and modifications may be made therein without departing from the spirit of the invention or from the scope of the appended claims.

What is claimed is:

1. A truck for transporting air under pressure to a remote site for rescue purposes comprising:

a truck, said truck comprising a frame having front, back, top, bottom and a pair of side panels attached thereto for defining an elongated hollow enclosure, said side panels being hingedly mounted to said frame for moving said side panels to similar open positions to expose common planar surfaces thereof, a pair of air reservoirs one mounted on each of said common planar surfaces, one of said reservoirs furnishing air under pressure to a rescue person for breathing purposes and at the same time furnishing air under pressure from the other of said reservoirs to the rescue person for power tool operation, at least a pair of runners spacedly mounted to extend longitudinally along said back panel of said enclosure, a roller journalled on said frame along the bottom edge of said bottom panel, and a lifting bar connected to said frame to extend longitudinally and axially thereof along a longitudinal axis and extending outwardly of said top panel for use in moving said truck to and from said site.

2. The truck set forth in claim 1 in further combination with:

means mounted on a control panel in said enclosure and connected to said reservoirs for separately regulating the air flow from each of said reservoirs.

3. The truck set forth in claim 1 in further combination with:

a pair of handles detachably and spacedly mounted on said frame to extend outwardly of said back panel on a side of said enclosure common with said roller.

4. The truck set forth in claim 1 wherein:

said panels and said frame are formed of soft material or metal which will not produce sparks when impacted by rocks or other hard surfaces.

5. The truck set forth in claim 1 wherein:

one of said reservoirs furnishing air at a first pressure to said rescue person for breathing purposes and the other of said reservoirs furnishing air at a second pressure to said rescue person for power tool operation.

6. The truck set forth in claim 2 in further combination with:

means for pivotally mounting said top panel to said frame, and a secondary panel for mounting said regulating means mounted in said enclosure juxta-positioned to said top panel for exposure to the user upon rotating said top panel.

* * * * *